United States Patent [19]

Mathers

[11] Patent Number: 4,865,991
[45] Date of Patent: Sep. 12, 1989

[54] METHODS FOR PARTITIONING OF ORGANIC FLAVOR COMPOUNDS

[75] Inventor: Jeremy J. Mathers, Prospect Heights, Ill.

[73] Assignee: Kraft, Inc., Glenview, Ill.

[21] Appl. No.: 136,696

[22] Filed: Dec. 22, 1987

[51] Int. Cl.[4] ............................................. G01N 33/02
[52] U.S. Cl. ...................................... 436/20; 436/161; 436/171; 436/194; 260/428.5; 512/5; 210/774
[58] Field of Search ............... 436/20, 178, 161, 52, 436/53, 164, 171, 174, 176; 260/428.5; 512/5; 210/774

[56] References Cited

U.S. PATENT DOCUMENTS

| 4,692,415 | 9/1987 | Rust | 436/20 |
| 4,705,690 | 11/1987 | Brand et al. | 426/590 |

FOREIGN PATENT DOCUMENTS

| 0885873 | 11/1981 | U.S.S.R. | 436/20 |
| 1120237 | 10/1984 | U.S.S.R. | 436/20 |
| 1201769 | 12/1985 | U.S.S.R. | 436/20 |

OTHER PUBLICATIONS

Lee et al, Journal of the Assoc. of Off. Agr. Chmsts, 9/56, "Improved Apparatus and Method . . . Volatile Oil Content of Spices".
Karweik et al, Analyt. Ch., vol. 51, No. 2, 2/79, pp. 319–320, "Spectrophotometric Determination of Secondary Amines".
Vassilaros et al, Anal Chem, vol. 54, No. 1, 1/82, pp. 106–112, "Capillary Gas Chromatographic . . . In Vertebrate Fish Tissue".
Datta et al, Food Tech., vol. XVI, No. 10, 1962, pp. 116–119, "Use of Gas Chromatography to Identify Geo. Origin of Some Spices".
Fore et al, J of Amer Oil Chmsts, vol. 47, No. 1, pp. 17–18, "Determination of Residual . . . Formamide Extraction Procedure".
Wong et al., "Simple Technique for Extracting Flavor Compounds from Fatty Foods", J. Dairy Science, vol. 51, (1968), pp. 1768–1769.
Fujinaga, T., et al., "Study of Solvent Synergism for the Selective Extraction. IV.", Bunseki Kagaku, vol. 33 (3), pp. 159–164 (1984).

*Primary Examiner*—David L. Lacey
*Assistant Examiner*—L. Johnson
*Attorney, Agent, or Firm*—Fitch, Even, Tabin & Flannery

[57] ABSTRACT

Methods for partitioning and analysis of flavor volatile and other organic components in a food or bioculture composition utilizing acetonitrile-water blends which are cooled to provide a phase and component separation.

15 Claims, 10 Drawing Sheets

CONTROL SEQUENCE FOR EXTRACTION SYSTEM

TIME (Minutes)

| DEVICE | 1 | | | | 5 | | | | | 10 | | | | |
|---|---|---|---|---|---|---|---|---|---|---|---|---|---|---|
| Sample Valve - 20 | 0 | 1 | 0 | 0 | 0 | 0 | 0 | 0 | 0 | 0 | 0 | 0 | 0 | 0 |
| Pump - 16 | 1 | 1 | 0 | 0 | 0 | 0 | 0 | 0 | 0 | 0 | 0 | 0 | 0 | 0 |
| Stirrer - 22 | 0 | 0 | 1 | 1 | 1 | 1 | 0 | 0 | 0 | 0 | 0 | 0 | 0 | 0 |
| Heater - 22 | 0 | 0 | 1 | 1 | 1 | 1 | 0 | 0 | 0 | 0 | 0 | 0 | 0 | 0 |
| Derivatizing Reag. Pump - 24 | 0 | 0 | 1 | 0 | 0 | 0 | 0 | 0 | 0 | 0 | 0 | 0 | 0 | 0 |
| Acetonitrile Pump - 32 | 0 | 0 | 0 | 0 | 0 | 0 | 1 | 0 | 0 | 0 | 0 | 0 | 0 | 0 |
| Cooling Coil - 22 | 0 | 0 | 0 | 0 | 0 | 0 | 1 | 1 | 1 | 1 | 0 | 0 | 0 | 0 |
| Organic Sampling Pump - 34 | 0 | 0 | 0 | 0 | 0 | 0 | 0 | 0 | 0 | 0 | 0 | 0 | 0 | 0 |
| Valve - 36 | 0 | 0 | 0 | 0 | 0 | 0 | 0 | 0 | 0 | 1 | 1 | 1 | 0 | 0 |
| Valve - 38 | 0 | 0 | 0 | 0 | 0 | 0 | 0 | 0 | 0 | 1 | 1 | 1 | 0 | 0 |
| Autosampler Inject | 0 | 0 | 0 | 0 | 0 | 0 | 0 | 0 | 0 | 0 | 0 | 1 | 0 | 0 |
| Cleanout Pump | 0 | 0 | 0 | 0 | 0 | 0 | 0 | 0 | 0 | 0 | 1 | 1 | 0 | 0 |

SEQUENCE FOR ENTIRE SYSTEM

- Sample
- Derivatize
- Add Acetonitrile
- Chill
- Sample Organic Layer
- Inject
- Collect Data (From Previous Run)

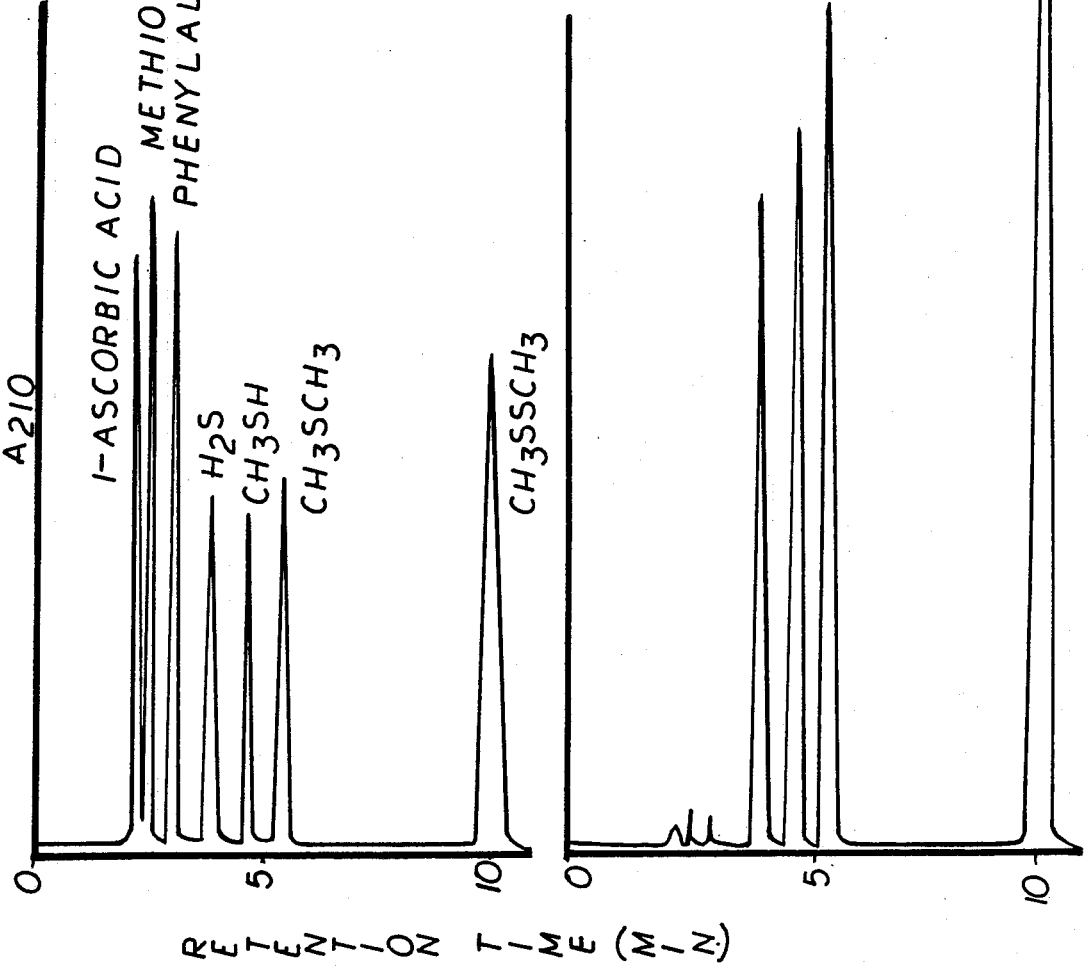
FIG.2. CHROMATOGRAPHY OF SULFER VOLATILES AND OTHER COMPOUNDS IN 50:50 ACETONITRILE:WATER MIXTURE(I) AND IN ORGANIC PHASE(II)AFTER PHASE SEPARATION AT-20°C.

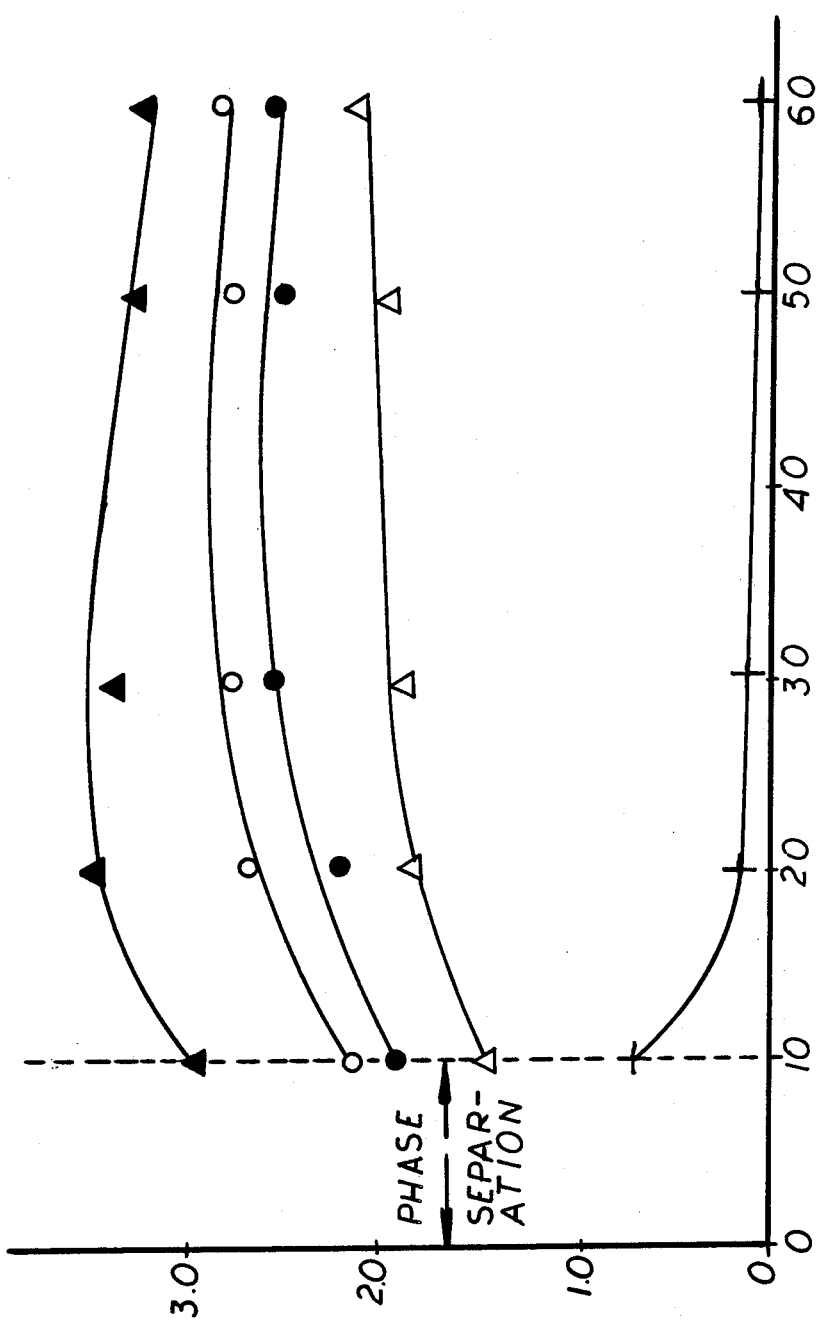

CORRELATION OF RP-HPLC RETENTION TIMES VS. PARTITION COEFFICIENTS FOR COMPOUNDS IN TABLE I. (●), BINARY PHASE SYSTEM, (O), TERNARY PHASE SYSTEM VALUES.

EFFECT OF TEMPERATURE AND ADDED CHLOROFORM ON ORGANIC/AQUEOUS VOLUME RATIOS. 3 ML ALIQUOTS OF A 1.1:1 ACETONITRILE:WATER MIXTURE AT 23°C WERE ADDED TO 4 ML VOLUME HPLC VIALS, AND THE VIALS WERE THEN SUBJECTED TO VARIOUS TEMPERATURES FOR 20 MINUTES. CHLOROFORM WAS ADDED TO TEST VIALS AT THE FOLLOWING LEVELS: (●) 0, (○) 0.01, (▲) 0.025, (△) 0.05, (■) 0.10, (□) 0.15 ML

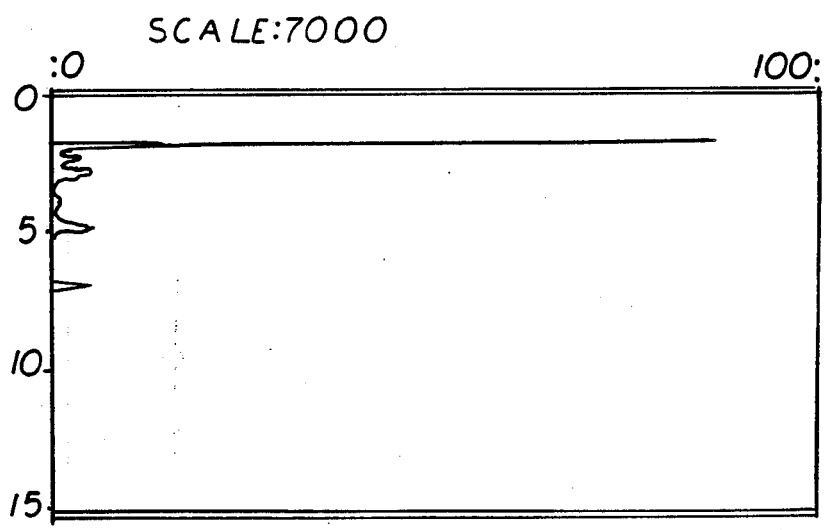
FIG. 6A BANANA, NONDERIVATIZED AT 210 NM
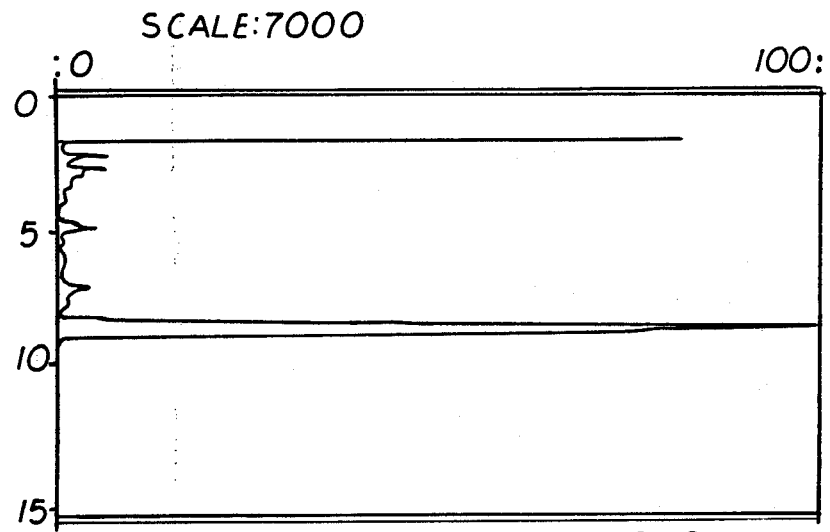
FIG. 6b BANANA, DERIVATIZED AT 210 NM
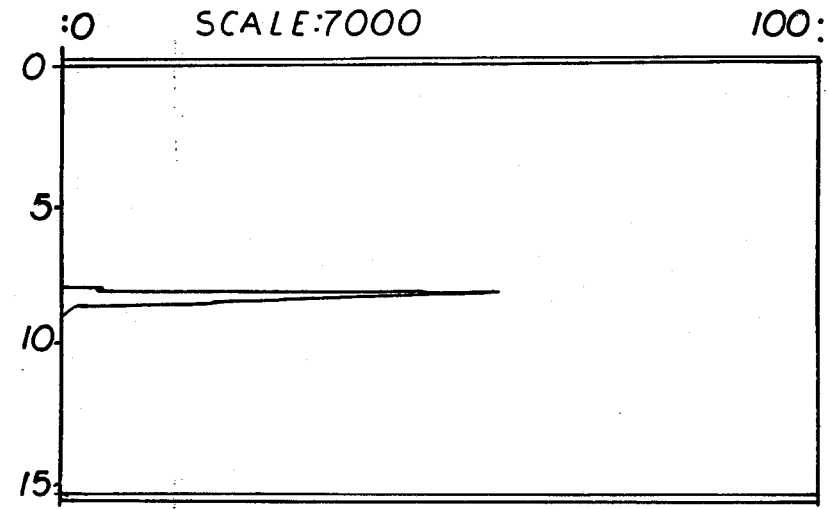
FIG. 6C BANANA, DERIVATIZED AT 320 NM

SHARP CHEDDAR CHEESE DERIVATIZED AT 320 NM

AMERICAN CHEESE SLICE DERIVATIZED AT 320 NM

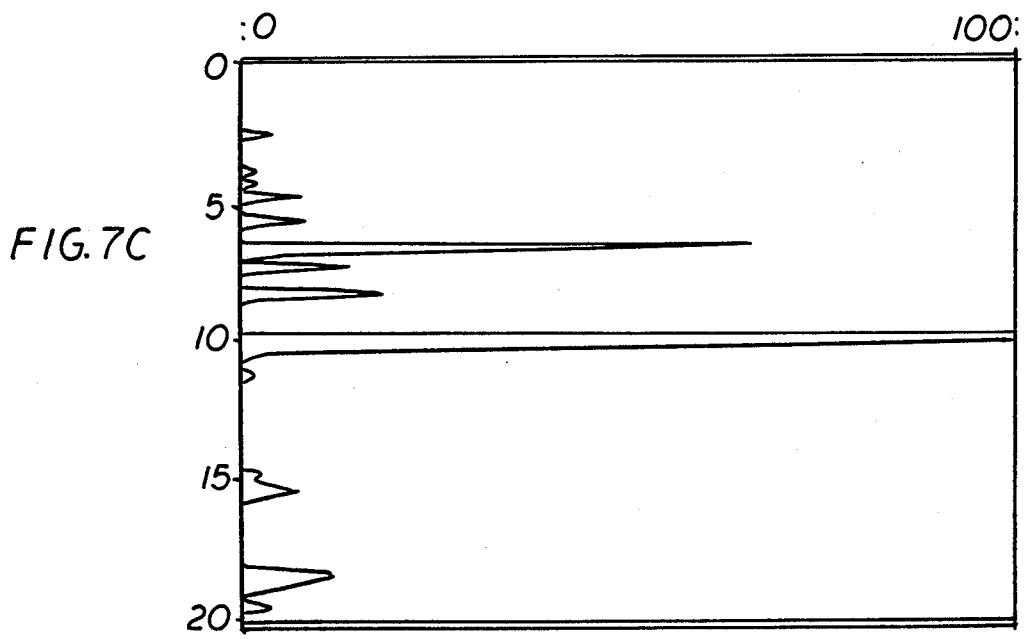
FIG. 7C
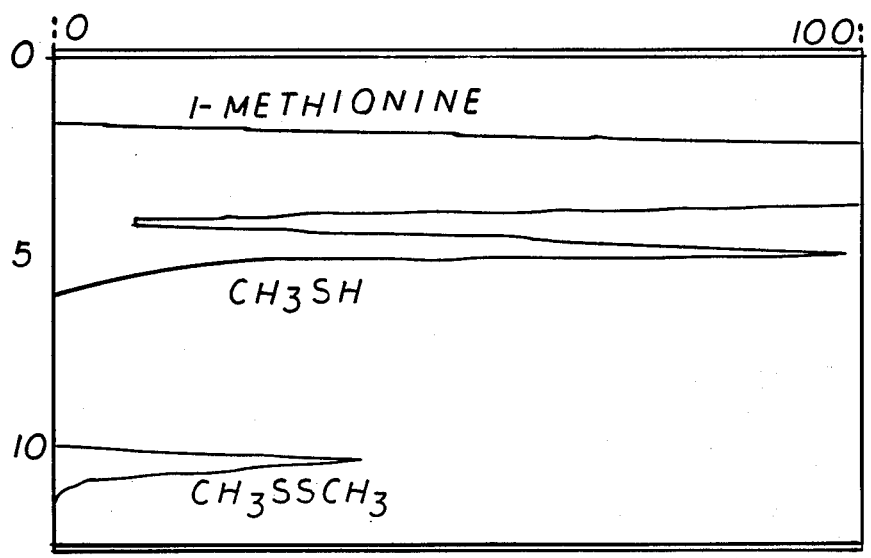
FIG. 8 RADIOISOTOPE DETECTOR CHROMATOGRAM OF METHANETHIOL AND DIMETHYLDISULFIDE PRODUCED BY BREVIBACTERIUM CASEI ATCC 35513 FROM THE AMINO ACID METHIONINE. THE TRACE LEVELS OF SULFUR VOLATILE COMPOUNDS WERE EXTRACTED INTO THE ACETONITRILE LAYER

METHODS FOR PARTITIONING OF ORGANIC FLAVOR COMPOUNDS

BACKGROUND OF THE INVENTION

The present invention is directed to methods and apparatus for analysis of organic flavor volatile components of food products. More particularly, the present invention is directed to methods and apparatus for phase separation extraction and quantitative or qualitative analysis of organic flavor volatile compounds of biological materials, such as food products.

Flavor volatile compounds, particularly including relatively nonpolar, flavor volatile organic compounds having less than 15 carbon atoms comprising at least one polarity-inducing element (e.g., oxygen, sulfur or nitrogen) are generally well known as important constituents of food products, which may profoundly or subtly affect their palatability and organoleptic characteristics. Very small amounts of flavor volatile components have an extremely important effect on the flavor and palatability of food products. Accordingly, in the preparation or testing of conventional food products, as well as in the development of new food products, it is desirable to analyze the food products, either quantitatively or qualitatively, for flavor volatile compounds. However, the quantitative and/or qualitative analysis of flavor volatile compounds in food products such as dairy products, is difficult because of the extremely small amount of such compounds in food products and the high content of potentially interfering materials in the food products. In this regard, for example, food products such as dairy products may typically contain major proportions of components such as fats, proteins, amino acids and salts which mask, dilute or otherwise interfere with flavor volatile assay.

Conventionally, various extraction methods for volatile organic flavor compounds are used in the analysis of flavor and fragrance, and in clinical studies. Distillation or trapping of volatile compounds using adsorbent materials, or organic phase separation using methylene chloride or other solvents are commonly utilized, each with respective advantages and disadvantages. In this regard, for example, one method for assay of flavor volatile compounds in cheese products involves comminution of the cheese product samples with a filler substrate such as a clay substrate to form an intimate substrate-cheese blend, and packing the blend into a column for subsequent extraction. Pure acetonitrile may be passed through the column, with flavor components being extracted into the acetonitrile [N. P. Wong, et al., J. Dairy Sci., 51 (1968) 1768–69].

There are many chemical and physical factors involved in the evaluation of extraction partitioning phenomena [A. Leo, et al., Chemical Reviews, 71 (1971) 525–616; H. Walter, et al., Anal. Biochem. 155 (1986) 215–242]. Phase partitioning by means of acetonitrile, water, and chloroform mixtures has been used to extract colored molybdophosphate complexes for colorimetric determinations in analysis of non-flavor inorganic materials [Fujinaga, T., et al., "Study of Solvent Synergism for the Selective Extraction. IV.", Bunseki Kagaku, Vol. 33 (3), pp. 159–164 (1984)]. However, such techniques have not been applied to quantitative or qualitative analysis of flavor volatiles in food products; moreover, the use of chloroform may interfere with known or unknown flavor volatile peaks. Both gas chromatography (GC) and high performance liquid chromatography (HPLC) have been used to identify and quantify organic compounds such as the sulfur volatiles [A. Tangerman, et al., Clin. Chim. Acta, 130 (1983) 103–110; A. Tangerman, J. Chromatogr., 366 (1986) 205–216; J. A. Cox, et al., Anal. Lett., 10 (1977) 869–885], with GC being preferred for determination of very low levels of such materials. Reverse phase HPLC retention times have been used to correlate n-octanol/-water partition coefficients [C.V. Eadsforth, Pest. Sci., 17 (1986) 311–325]of many compounds. However, while GC and HPLC analytical techniques are well developed which are suitable for detection and quantitation of specific organic compounds, conventional methods for food sample preparation and extraction of flavor volatile compounds have significant disadvantages.

New methods for assay of organic flavor volatile compounds which provide effective and convenient extraction of flavor volatile compounds from food products while minimizing interfering or masking components would be desirable, and it is an object of the present invention to provide such methods. New methods for extraction of selected polar components of biological fermentations would also be desirable, and it is similarly an object of the present invention to provide such methods. It is a further object of the invention to provide automated methods for organic flavor component analysis which may be readily and conveniently used in repetitive analytical testing systems. These and other objects of the inventions will be apparent from the following detailed description and the accompanying drawings.

DESCRIPTION OF THE DRAWINGS

FIGS. 2a and 2b are graphical illustrations of the overall partitioning/concentrating effect on the high performance liquid chromatography of four sulfur volatiles and 1-methionine;

FIG. 3 is a graphical representation of the time course for selected temperature of −20° C. of the compounds of FIG. 2;

FIGS. 6a, 6b and 6c are HPLC chromatograms for natural and derivatized organic flavor volatile compounds of ripe banana, utilizing an acetonitrile/water phase partitioning process in accordance with the present invention;

FIGS. 7a, 7b and 7c are HPLC chromatograms for derivatized organic flavor volatile compounds of sharp cheddar cheese, American cheese and blue cheese, respectively, utilizing an acetonitrile/water phase partitioning process in accordance with the present invention; and FIG. 8 is a chromatogram of radiolabelled flavor components methanethiol and dimethylsulfide produced by a bacteria and analyzed by utilizing an acetonitrile/water phase partitioning process in accordance with the present invention.

DESCRIPTION OF THE INVENTION

Figure 1A:
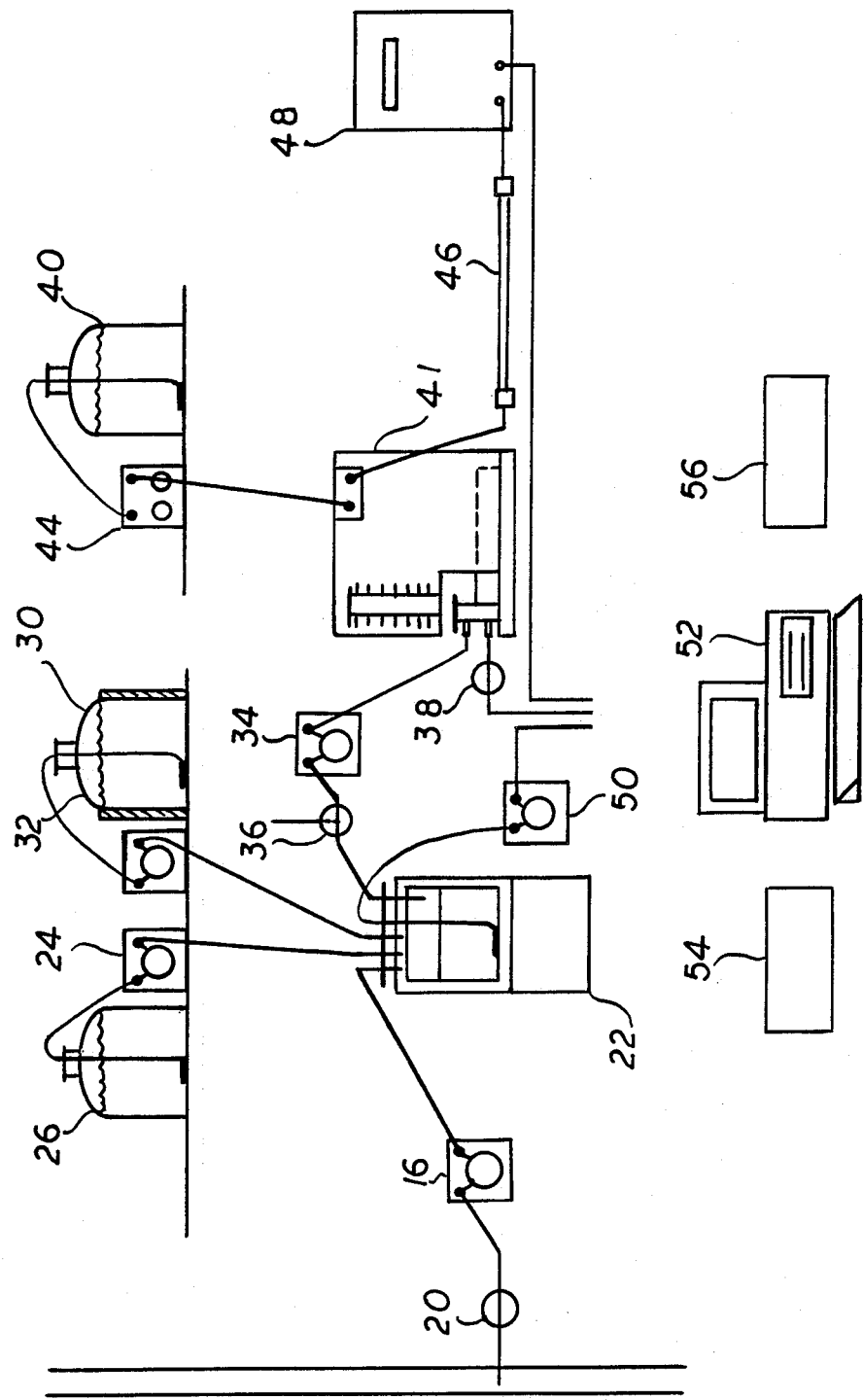
FIGURES 1a, 1b and 1c are schematic illustrations of analytical apparatus suitable for automated flavor volatile analysis in accordance with an embodiment of the present invention together with timing charts for operation of the apparatus.
Figures 1B, 1C:
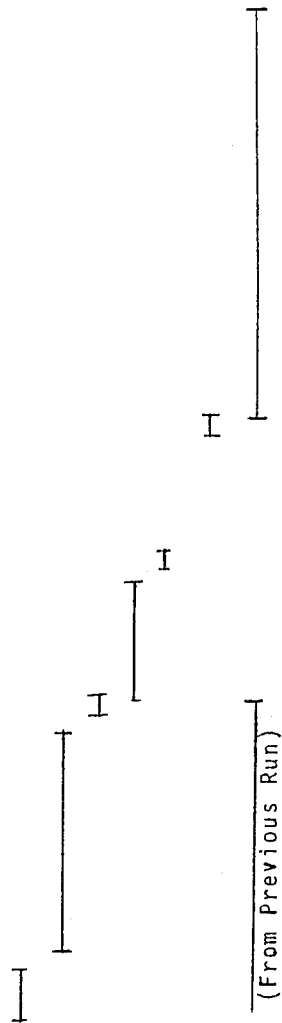

Generally in accordance with the present invention, methods are provided for partitioning and analysis of flavor volatile compounds in a food composition. By organic flavor compound, such as an organic flavor volatile compound, is meant a polar organic compound, which is a constituent of a food product or a bioculture composition or product, having less than 15 carbon atoms and comprising at least one element selected from the group consisting of oxygen, sulfur and nitrogen. As used herein, the term organic flavor compounds includes derivatized flavor compounds, such as 3-methyl-2-benzothiazolinone hydrazone derivatives of ketone flavor volatile compounds. Derivatizations may be utilized to modify or improve separation and/or detection characteristics.

The food composition may be any edible food product, mixture of food products or biological material for which flavor component analysis is desired. Such food compositions may comprise carbohydrate-rich foods such as cereals and grains (e.g., rice, oats, barley, corn and wheat), protein-rich foods such as meat, poultry, fish, eggs, legumes, nuts and dairy products (e.g., milk, natural cheese, process cheese, cottage cheese and cream cheese), lipid-rich foods such as butter and vegetable oils, vegetables and fruits, edible seasonings and flavorings, as well as mixtures, blends and prepared combinations of such food compositions. Various aspects of the present methods are also directed to component separation or assay of biological culture or fermentation products, herein referred to as "bioculture compositions" (which may also be food products or compounds of food products). Examples of bioculture compositions are bacterial, animal, yeast or other plant cell cultures in which one or more polar organic compounds is elaborated or produced by the culture. Included in this term are hydrolysis products and derivatives of sequential or stepwise hydrolysis products of cell components and products, which may be separated by methods in accordance with the present invention for genetic engineering or purification purposes.

In accordance with various aspects of the present invention, the food composition or bioculture product is dispersed in a fluid mixture of acetonitrile and water to provide a fluid food composition dispersion at a preselected dispersion-extraction temperature in the range of from about 10° C. to about 100° C. The food composition may be dispersed in an acetonitrile/water mixture by any suitable mixing technique such as dissolution, homogenization, maceration and/or high or low shear blending or milling in admixture with a fluid acetonitrile-water mixture. The acetonitrile-water mixture will consist essentially of acetonitrile and water. Desirably, the acetonitrile mixture will be substantially free of other solvent components, but in various applications, small amounts of other solvent components may be included if they do not interfere with the analysis or extraction. Generally, appropriate amounts of the food or bioculture composition, water and acetonitrile will be combined to provide a fluid food composition and/or bioculture composition dispersion having from about 10 to about 50 percent by weight of nonaqueous food or bioculture solids and from about 50 to about 90 weight percent of acetonitrile, based on the total weight of the fluid food and/or bioculture composition dispersion. It will be appreciated that the food or bioculture composition itself may be anhydrous (e.g., certain dried or lipid based food products) or, more typically, may contain a substantial amount of water. The amount of water in the food or bioculture composition product, and the affinity of the food or bioculture composition for water, will be a factor in the determination of the respective amount of water (if any) and acetonitrile to combine with the food or bioculture composition to form the dispersion with acetonitrile and water.

The acetonitrile and water components of the fluid food or bioculture composition dispersion form a homogeneous solution at ambient temperature which functions as a solvent for the flavor volatile compounds of the food composition. Because the food composition is intimately distributed in the acetonitrile-water solution, a rapid and highly efficient extraction of such compounds to the acetonitrile-water phase is accomplished in the fluid food composition dispersion.

After forming the dispersion, the dispersion is cooled at least about 5° C., and preferably at least about 25° C. to a temperature of less than about −10° C., which is sufficient to cause a phase separation of the acetonitrile-water solution to produce an acetonitrile-rich phase containing flavor volatile compounds of the food composition and a separate water rich phase containing food composition components depleted in flavor volatile components.

The phase separated mixture should best be maintained at a phase separation temperature of less than about −10° C. under quiescent conditions for a period of time, preferably at least about 10 minutes, which is sufficient to separate the phases into two distinct layers, the water-rich phase, and the acetonitrile-rich phase, respectively. By "quiescent conditions" is meant non-turbulent conditions suitable for phase coalescence. Such phase coalescence may be carried out in a vessel suitable for phase separation, preferably with a height to width ratio greater than one, in a fixed position with little or no agitation during the phase separation time. Alternatively, a countercurrent extraction apparatus may be used with similar temperature and acetonitrile/water ratios. The layer formation may be enhanced by centrifugation under quiescent conditions if desired.

Generally, the acetonitrile-rich phase will comprise at least about 85 weight percent of acetonitrile, and less than about 15 weight percent of water, based on the total weight of the acetonitrile-rich phase. Similarly, the water-rich phase will generally comprise at least about 80 weight percent of water and less than about 20 weight percent of acetonitrile, based on the total weight of the separate water-rich phase. The phase separation and layer formations may be carried out to provide a clarified acetonitrile layer substantially free of undissolved food components, which is suitable for direct utilization in subsequent analytical procedures such as high performance liquid chromatography (HPLC) or gas chromatography (GC).

Methods in accordance with the present invention may be readily automated. In this regard, an embodiment of an online acetonitrile organic component extractor and quantitative analysis system 10 is illustrated in FIG. 1a.

The illustrated device 10 functions to obtain a liquid sample of a food product, such as from a process stream, which sample is derivatized if necessary. The sample is extracted using a binary aqueous/acetonitrile phase separation, and analyzed directly by an HPLC, GC, FIA, or other suitable analytical instrument, without the need for extensive filtration, solid phase extraction, or other methods of sample clean up. The acetonitrile selectively extracts nonpolar materials from polar, ionic and high molecular weight compounds, and may be directly injected onto an analytical device such as a high performance liquid chromatograph. The analysis of compounds which normally would be excluded in the organic extraction (e.g., low molecular weight carbonyl compounds) is facilitated by using a derivatizing reagent such as 3-methyl-2-benzothiazolinone, which forms a less polar derivative of the compound, which is then selectively extracted into the organic phase of a binary system. The acetonitrile phase is formed by subjecting the mixture to low temperature and therefore has no additional compounds which may interfere with the analysis.

The operation of the device 10 of FIG. 1a begins when a liquid sample 12 from a process stream 14 is drawn by pump 16 and directed to sample line 18. After the sample volume has entered the line 18, valve 20 actuates, causing air to follow and propel the sample into the extraction vessel 22. If the sample requires derivatization, pump 24 adds the required volume of derivatizing reagent from reservoir 26. Temperature and stirring are controlled in vessel 22 by means of appropriate cooling coils, stirrer and/or heater assemblies of the vessel 22 to complete the derivatization step.

The proper volume of cold acetonitrile (−20° C.) is then added from reservoir 30 by pump 32 to a preselected ratio (1:1 or greater). Stirring continues and the temperature is maintained at −20° C. by means of the cooling coil assembly of the vessel 22 for a preselected time period to completely chill the sample (1 to 10 minutes), stirring is then stopped, and the acetonitrile phase separates from the aqueous material, extracting the low molecular weight (e.g., less than 150 daltons) nonpolar and aromatic compounds to be analyzed.

A 3 ml sample of the organic phase is then drawn off by pump 34. After the sample has entered the line, valves 36 and 38 actuate, causing air to propel the sample into the HPLC sampling vial in the autosampler 40. The autosampler then injects a precise amount (5-100 microliters) into the analytical system, such as a high performance liquid chromatograph comprising a liquid mobile phase in reservoir 42, HPLC pump 44, autosampler 40, analytical column 46 and UV detector 48, in accordance with conventional practice.

After the injection, valve 38 actuates and pump 34 runs, forcing the sample out to a waste receptacle. Pump 34 then stops and valve 36 actuates, resetting it. Pump 50 runs, clearing the extraction vessel, then stops, completing the operational cycle.

Computer 52 is shown along with extraction system interface 54 and analytical interface 56. The computer system may be any data acquisition/control configuration capable of running the extraction system based on programmed events timing, as well as the analytical system. Alternatively, a separate microprocessing system may run the analytical device and optionally send the data via standard data transmission and protocols to computer 52.

Tables 1b and 1c accompanying FIG. 1a describe a control matrix used to implement computer control of the extraction system, and the overall running of the complete system. The timing values and sequences are approximate and may be changed to accommodate different extractive steps, analytical devices or analysis times desired.

Having generally described various aspects of the present invention, specific embodiments of such methods and apparatus will now be more particularly described which utilize a partition between acetonitrile and water at low temperature, using reverse phase HPLC to determine overall organic phase partitioning of some lower molecular weight sulfur and other organic volatiles.

EXAMPLE 1

Figure 4A:
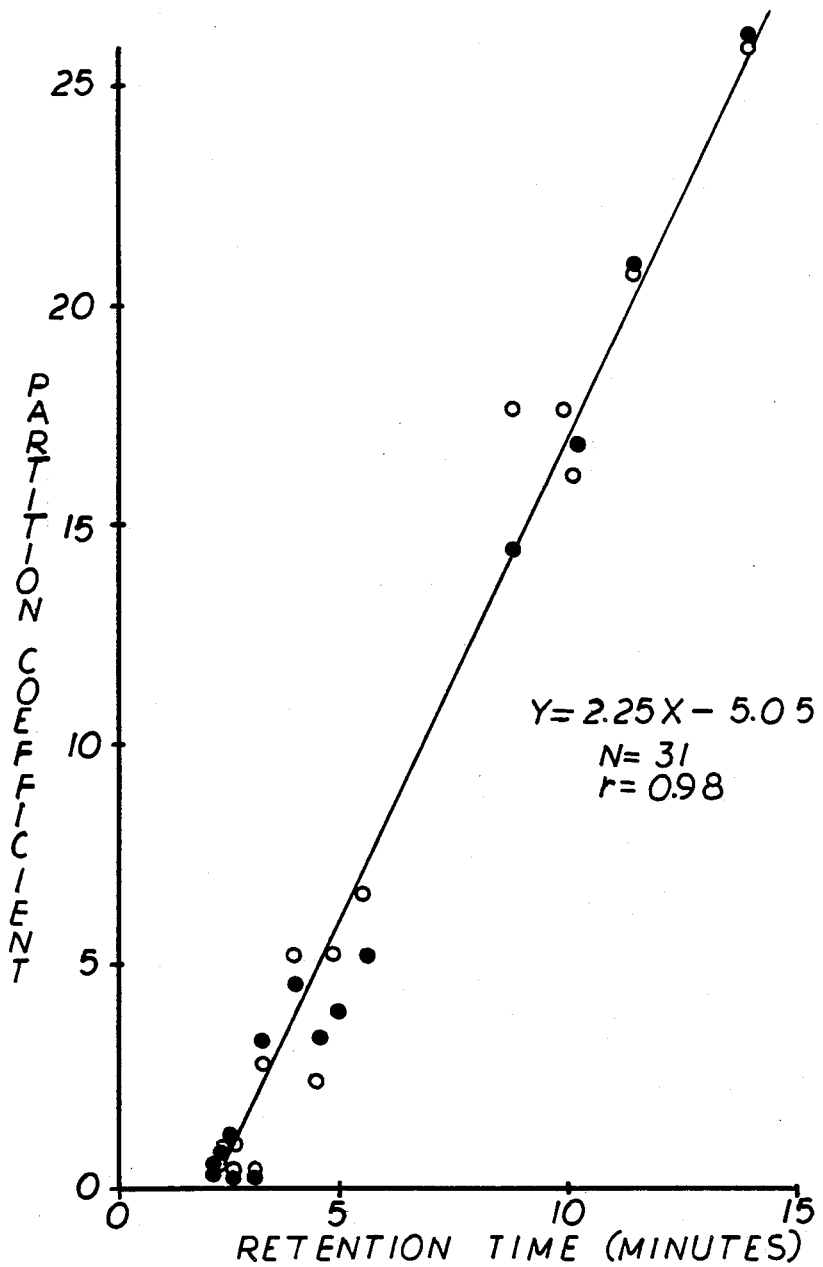
FIG. 4a is a graphic representation of retention time and organic phase partitioning relationships for a variety of organic flavor volatile and other compounds of Table 1.

In these tests, known organic flavor volatile compounds were added to 2 ml aliquots of 50:50 acetonitrile:water, 22° C., in 4 ml HPLC vials, mixed thoroughly and capped with polytetrafluoroethylene septum caps. The compound levels varied from 0.02 to 1.0% w/v or v/v to give equivalent UV detector responses. The samples were injected (20 uL) into a continuous HPLC apparatus. The separation technique utilized is a phase separation of a nominal 1:1 acetonitrile:water system, which formed separate phases in 10 minutes at −20° C. This separation effectively partitioned organic volatile compounds from fats, proteins, amino acids and salts, making it suitable for chromatography sample preparation. Reverse phase high performance liquid chromatography (HPLC) was used to determine the partition coefficient, for several organic volatiles and the minimum time required for complete partitioning (1 hour). Organic partitioning was related to HPLC retention times as shown in FIG. 4a. Samples could be held for 24 hours with no significant change. The HPLC apparatus was a Waters WISP model 710B sample injector, 6000A pump, and 481 UV detector set at 210 nm (Waters Associates, Milford, MA). A Radiomatic Flo-One Beta unit was used for peak integration (Radiomatic Instruments, Inc., Tampa FL). An Alltech adsorbosphere C18 column, 5 micron, 250 mm×4.6 mm was used (Alltech Associates, Deerfield, IL) to achieve component separation in accordance with conventional HPLC processing. The mobile phase had the following composition: 45% acetonitrile, 55% water, 0.2% $KH_2PO_4$, pH 3.0. The flow rate was 1.0 ml/minute. The vials were then placed in a freezer (−20° C.) for one hour. 250 uL of the resulting organic and aqueous phases were then placed in a limited volume insert vial, the sample injected and peak integrations acquired. The partition coefficient, P, was calculated by dividing the organic phase by the aqueous phase integration values.

To determine the time period appropriate for complete partitioning, four sulfur volatiles and 1-methionine were treated as above, except that samples were taken at different times up to 60 minutes FIGS. 2a, 2b and 3).

Table 1 lists the retention times and partition coefficients calculated for several organic volatile and nonvolatile compounds.

TABLE 1
RETENTION TIMES AND PARTITION COEFFICIENTS FOR ORGANIC COMPOUNDS IN ACETONITRILE PHASE SYSTEMS

| Compound | Retention Time (Min) | Partition Coefficient Binary[a] | Partition Coefficient Ternary[b] |
|---|---|---|---|
| Ethyl Valerate | 13.8 | 25.9 | 25.6 |
| Caprylic acid | 11.2 | 20.8 | 20.6 |
| Dimethyl disulfide | 9.9 | 16.7 | 17.7 |
| Chloroform | 9.9 | — | 16.2 |
| Ethyl Butyrate | 8.7 | 14.3 | 17.6 |

TABLE 1-continued

RETENTION TIMES AND PARTITION
COEFFICIENTS FOR ORGANIC COMPOUNDS IN
ACETONITRILE PHASE SYSTEMS

| Compound | Retention Time (Min) | Partition Coefficient Binary[a] | Partition Coefficient Ternary[b] |
|---|---|---|---|
| Dimethyl sulfide | 5.4 | 5.2 | 6.6 |
| Methanethiol | 4.7 | 4.0 | 5.2 |
| 2-phenyl ethanol | 4.3 | 3.3 | 2.3 |
| Hydrogen sulfide | 3.9 | 4.6 | 5.2 |
| Butyric acid | 3.2 | 3.1 | 2.7 |
| 1-phenylalanine | 2.8 | 0.1 | 0.3 |
| 1-methionine | 2.5 | 0.03 | 0.2 |
| acetic acid | 2.5 | 1.1 | 0.9 |
| lactic acid | 2.3 | 0.6 | 0.8 |
| 1-galactono-1,4-lactone | 2.1 | 0.2 | 0.2 |
| 1-ascorbic acid | 2.1 | 0.4 | 0.3 |

[a]Acetonitrile/water 1:1, 1 hr. at −20° C.
[b]Acetonitrile/water/chloroform 5:5:1, 22° C.

Amphiphatic compounds (amino acids) partitioned to the aqueous phase while the relatively less polar volatile compounds exhibited organic partitioning. Organic acids with straight chain overall structure up to $C_8$ partition in the acetonitrile-rich phase. Higher molecular weight straight chain acids were insoluble at the low temperature and accumulated at the interface. Nonpolar aromatic compounds with molecular weights of 250 Daltons or less were selectively extracted to the acetonitrile-rich organic phase, presumably due to pi-pi bond interaction of the aromatic ring with the nitrile group of acetonitrile. There was a relationship between HPLC retention times and organic partitioning as shown in FIGS. 2-4. The more nonpolar compounds, with retention times of 8 or more minutes, strongly partitioned to the organic phase with partition coefficients greater than 10.

Figure 4B:
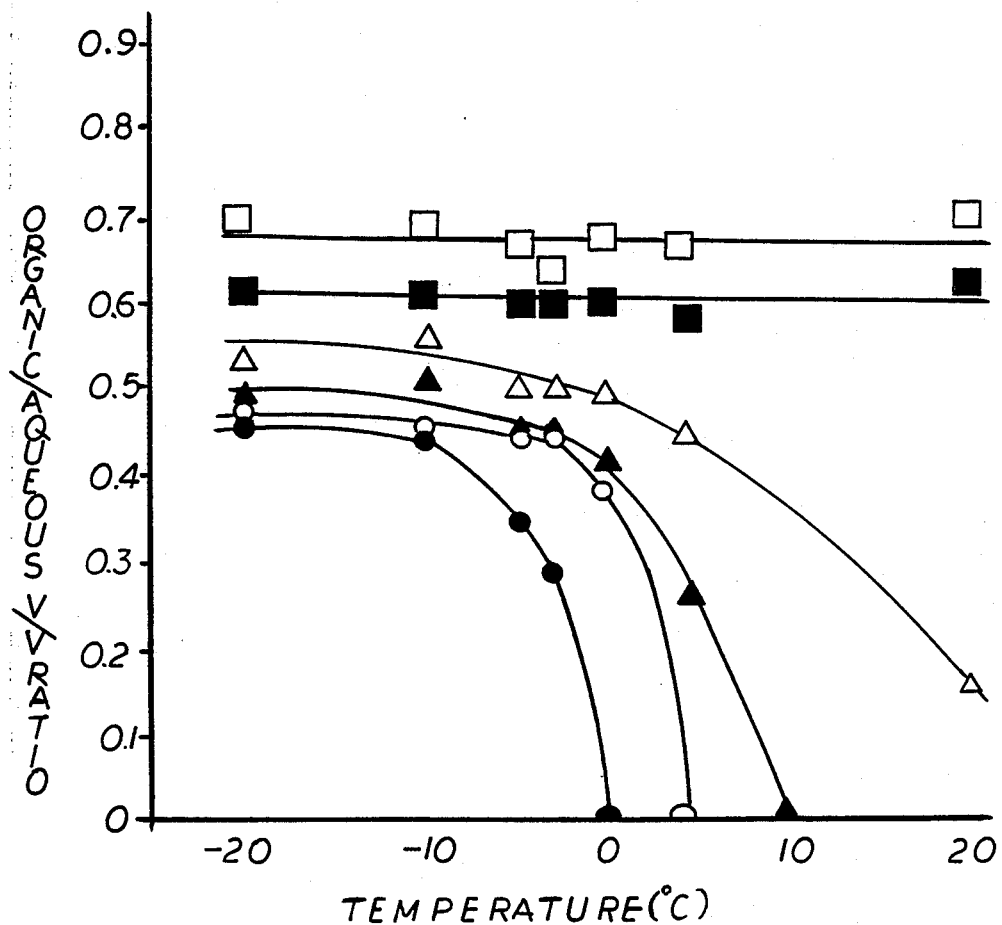
FIG. 4b shows the relationship of temperature to volumetric partitioning of the acetonitrile, with and without added levels of chloroform.

FIGS. 4a and 4b, and Table 1 show that the partition coefficient (P) of organic compounds in the binary (acetonitrile and water only) phase system is independent of temperature and the organic/aqueous volume ratio. Data points describing phase characteristics for the ternary system (acetonitrile, water and chloroform) are included in the table and figures for comparison purposes. The levels of chloroform added may cause interference in the chromatographic qualitative and quantitative analysis.

Acetonitrile/water is a very good solvent for most polar and nonpolar low molecular weight organic compounds. The described partitioning method has been utilized for rapid extraction and concentration of volatiles from more complex aqueous materials for analysis by HPLC or other systems. Clear organic phases suitable for direct injection were obtained from microbiological growth media with cells, and from foods.

EXAMPLE 2

This example illustrates the extraction of caffeine from cola beverage using cold, aqueous partitioning of an acetonitrile solution of a cola beverage.

A commercially available cola beverage (Pepsi) was used to demonstrate selective extraction of the relatively nonpolar organic compound caffeine using the binary phase extraction. 1.5 ml of the cola was placed in a 3 ml vial, and 1.7 ml of acetonitrile. The sample was shaken for 20 seconds and was chilled to −20° C. for 1 hour. 0.3 ml of the organic layer was then placed in an HPLC sampling vial. The HPLC system used was: a phenyl reversed phase column (Alltech Associates, Deerfield, Ill.) 250×4.6 mm, 5 micron. 25% acetonitrile, 75% water 0.2% w/v $KH_2PO_4$, pH 3.0 mobile phase, 1.5 ml/min. flow rate 20 uL injection by the autosampler. UV detection at 210 nm.

Figure 5A:
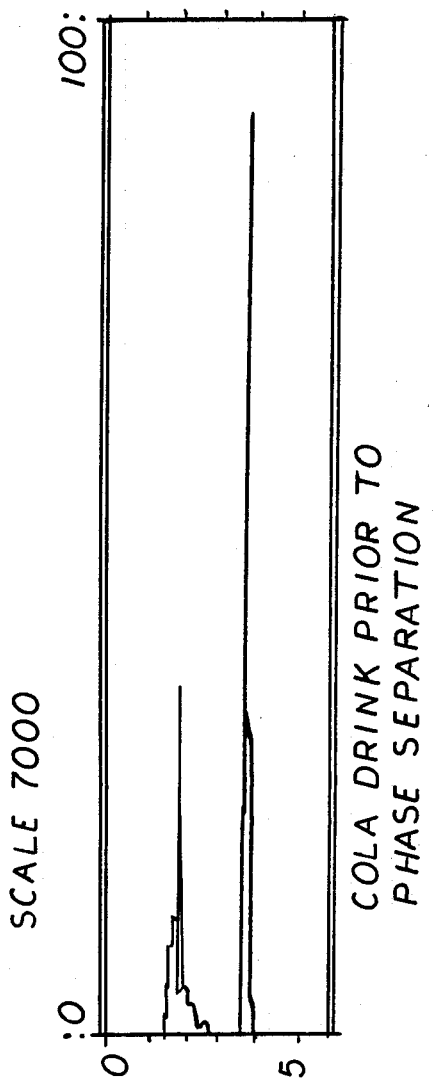
FIGS. 5a and 5b are HPLC response curves for caffeine and other polar compounds of a commercial cola beverage prior to and after phase separation in a water-/acetonitrile system.
Figure 5B:
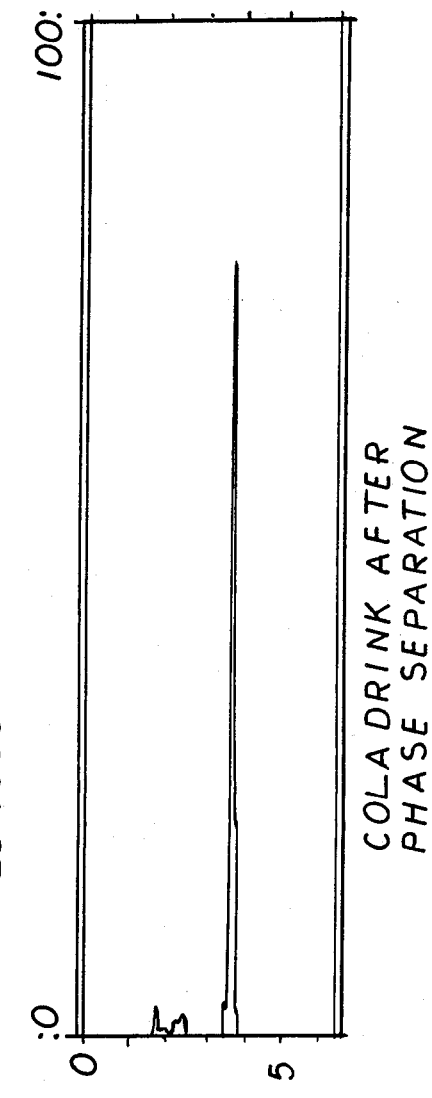

FIG. 5a is a chromatogram of the original cola plus acetonitrile mixture prior to cold phase partitioning. The chromatogram in FIG. 5b is of the organic phase after cold phase partitioning. Caffeine (retention time 3.7 minutes) is selectively extracted into the organic phase, while the other polar and ionic compounds are excluded.

EXAMPLE 3

This example illustrates the extraction of a keto acid derivative from ripe banana through the use of cold partitioning of an aqueous acetonitrile slurry of the banana.

In two 20 ml. volume vessels, 5 gm each of ripe banana material was blended with 5 ml distilled water and 7 ml acetonitrile. To one was added 1 ml of (0.4% w/v) 3-methyl-2-benzothiazolinone hydrazone (MBTH), a derivatizing agent for keto compounds. Both vials were placed at 50° C. for 30 minutes for the derivatization reaction. They were then chilled to −20° C. and held for 1 hour. 0.3 ml of the organic phase was placed in a HPLC vial and 20 uL injected into the HPLC system described previously. FIGS. 6a and 6b quantitatively show the amount of underivatized and derivatized samples, respectively, measured at 210 nm UV absorption wavelength. Smaller peaks represent nonpolar compounds extracted directly from the banana pulp. The large peak present in the derivatized sample is presumed to be the derivative of a keto compound. FIG. 6c is another chromatogram of the derivatized sample, detected at 320 nm UV, a wavelength at which the MBTH-keto linkage absorbs. The chromatogram shows that the peak at 8.3 minutes is an MBTH derivative. The compound was presumptively identified as oxaloacetic acid. The oxaloacetic acid would normally have been excluded from the organic phase, but the selective derivatization step produced a nonpolar compound which is selectively extracted into the organic phase.

EXAMPLE 4

This example illustrates the extraction of Keto flavor compound derivatives from cheese through the use of cold partitioning of an aqueous acetonitrile slurry of the cheese.

Figure 7A:
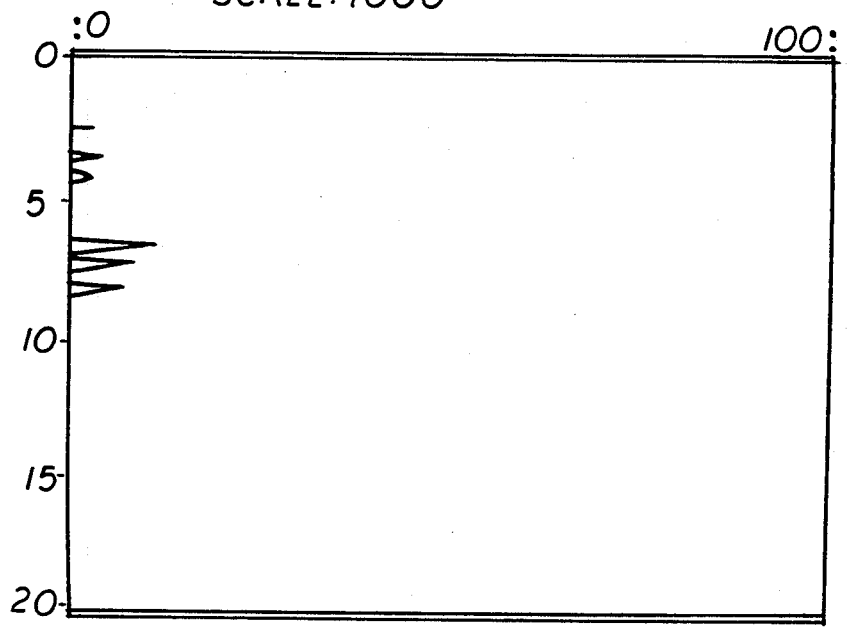
Figure 7B:
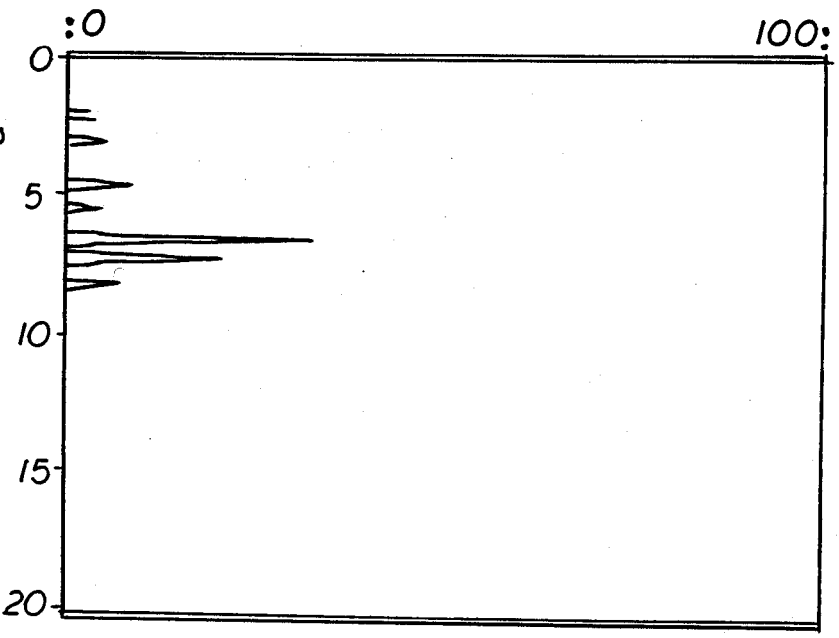

Three 20 ml volume vessels were used. 5 gm each of a sharp cheddar cheese, American cheese and blue cheese were blended with 5 ml distilled water and 7 ml of acetonitrile. To each, 1 ml of (0.4%) MBTH solution was added. The samples were thoroughly mixed and were held at 50° C. for 30 minutes to complete the derivatization step. The samples were then chilled to −20° C. for 1 hour. 0.3 ml of the organic phase was placed in a HPLC sample vial and 20 uL were injected on the HPLC system described previously. FIGS. 7a, 7b and 7c are the absorption chromatograms of the three cheese types, at 20 nm to absorption wavelength exclusively detect the MBTH-keto derivatives. American and cheddar cheese samples appeared to have similar kinds of keto acids, in different quantities. Two of the compounds were presumptively identified as glyoxylic and pyruvic acid derivatives. Blue cheese is shown to have at least five additional keto compounds present. This is consistent with current knowledge that blue cheese flavor is derived largely from keto acids especially 7-heptanone which is present at the highest level in the blue cheese sample and is known to be a major contributing component of blue cheese flavor. The pyruvic and glyoxylic acids would normally have been excluded from the organic phase, but the selective derivatization produced nonpolar derivatives which were readily extracted by the acetonitrile.

EXAMPLE 5

This example illustrates the use of reducing temperature phase separation with biological cells for analytical purposes and biocomponent extraction, recovery or analysis. In this regard, biological cultures of bacteria, plant or animal cells may be processed with or without disruption of the cell wall, to clarified, partitioned layers comprising an acetonitrile-rich layer containing extracted components and a water-rich layer containing the bacteria, proteins and other cellular materials.

Brevibacterium species are commonly used for limburger and other surface-ripened cheeses. It is known that species such as *B. linens* possess methionine lyase enzyme [E.C.C. 4.4.11] which cleaves the amino acid l-methionine in the cheese to methanethiol, a flavor compound contributing a strong oniony or garlicy smell and taste in cheeses [Ferchichi, M., et al., J. General Microbiology, 131, pp. 715-723 (1985)]. Quantitation of the methanethiol produced from methionine by a growing culture of a *B. casei* in nonoptimized growth medium was done using an HPLC system with both ultraviolet and radioisotope detectors. 5 mM nonradioactive l-methionine was added to 1 ml of the APT medium along with $2.0 \times 10^7$ cpm 35S-methionine. A 1.0% inoculum of *B. casei* ATCC 35513 was added to the medium, and the vial was capped with a septum seal. The vial was incubated for 3 days at 30° C. Trace levels of methanethiol and dimethyldisulfide (the oxidation product of methanethiol) were produced by the slowly growing culture 1.2 ml of pure acetonitrile was injected through the septum and the sample was briefly vortexed. The sample was then held at −20° C. for one hour. The organic phase was clear and free of cell debris. 250 ul of the sample was removed and placed in a limited volume HPLC vial. Quantitation of the sulfur flavor compounds was accomplished using the HPLC system and partition coefficients described earlier for the same sulfur compounds. FIG. 8 shows the radioisotope detector chromatogram of the organic phase. Methanethiol and dimethyl disulfide were detected at ppm levels.

While the present invention has been described with particularity with respect to specific embodiments, it will be appreciated that various modifications and adaptations may be made based upon the present disclosure, which are intended to be within the spirit and scope of the present invention.

What is claimed is:

1. A method for partitioning and analyzing flavor volatile or other polar organic compounds in a food or bioculture composition comprising the steps of
    dispersing a food or bioculture composition in a fluid mixture of acetonitrile and water to provide a fluid composition dispersion,
    cooling said dispersion to a phase separation temperature which is sufficient to cause a phase separation of the fluid mixture of acetonitrile and water to produce a phase-separated mixture of an acetonitrile-rich phase containing flavor volatile or other polar organic compounds of the food or bioculture composition and a water-rich phase containing the composition components depleted in said flavor volatile or other polar organic compounds, wherein said acetonitrile-rich phase comprises at least about 85% of acetonitrile and less than about 15 weight percent of water based on the weight of the acetonitrile-rich phase,
    maintaining said phase-separated mixture at a phase separation temperature under quiescent conditions to separate said acetonitrile-rich and said water-rich phases into two distinct layers, a clarified acetonitrile-rich layer containing said flavor volatile or other polar organic compounds of the food or bioculture composition and a water-rich layer containing food or bioculture composition components depleted in said flavor volatile or other polar organic flavor compounds, and
    analyzing at least a portion of the acetonitrile-rich layer for said flavor volatile or other polar organic compounds.

2. A method in accordance with claim 1 wherein said analyzing step is carried out by high performance liquid chromatography.

3. A method in accordance with claim 1 wherein said analyzing step is carried out by gas chromatography.

4. A method in accordance with claim 1 wherein said analyzing step is carried out by flow injection analysis, spectroscopy or polarography.

5. A method in accordance with claim 1 wherein said fluid food or bioculture composition dispersion comprises from about 10 to about 50 weight percent of food or bioculture solids and from about 50 to about 90 percent by weight of acetonitrile based on the total weight of said dispersion, and wherein said water-rich phase comprises at least about 80 weight percent of water and less than 20 percent of acetonitrile based on the total weight of the water-rich phase.

6. A method in accordance with claim 1 wherein said dispersion is cooled at least about 5° C. to a phase separation temperature of less than about −10° C.

7. A method in accordance with clam 1 wherein the ratio of water to acetonitrile in said fluid food composition dispersion is about 1:1.

8. A method in accordance with claim 1 wherein said dispersion is cooled at least about 25° C. to a phase separation temperature of less than about −10° C.

9. A method in accordance with claim 1 wherein said organic flavor compounds are derivatized prior to said cooling step.

10. A method in accordance with claim 9 wherein the derivatizing agent employed in the derivatizing step is the keto flavor derivatizing agent 3-methyl-2benzothiazolinone hydrazone.

11. A method in accordance with claim 1 wherein said dispersion is cooled at least about 25° C. to a phase separation temperature of less than about −10° C.

12. A method in accordance with claim 11 wherein said phase separation mixture is maintained at a phase separation temperature of less than about −10° C. under quiescent conditions for at least about 10 minutes.

13. A method in accordance with claim 12 wherein said separation of phases into two distinct layers is carried out by centrifugation under quiescent conditions.

14. A method for component separation of a bioculture composition containing one or more polar organic compounds elaborated or produced by a bacterial, animal, yeast or plant cell culture of the bioculture composition comprising the steps of dispersing said bioculture composition in a fluid mixture of acetonitrile and water to provide a fluid bioculture composition dispersion, cooling the dispersion to a phase separation temperature which is sufficient to cause a phase separation of the fluid mixture of acetonitrile and water to produce a phase-separated mixture of an acetonitrile-rich phase containing organic compounds of the bioculture composition and a water-rich phase containing bioculture composition components depleted in said organic compounds, wherein said acetonitrile-rich phase comprises at least about 85% of acetonitrile and less than about 15 weight percent of water based on the weight of the acetonitrile-rich phase, maintaining said phase-separated mixture at a phase separation temperature under quiescent conditions to separate said acetonitrile-rich and said water-rich phases into two distinct layers, a clarified acetonitrile-rich layer containing polar organic compounds of the bioculture composition and a water-rich layer containing bioculture composition components depleted in said polar organic compounds, and separating said layers for purification of said polar organic compounds.

15. A method in accordance with claim 14 wherein said fluid bioculture composition dispersion comprises from about 10 to about 50 weight percent of bioculture composition solids and from about 50 to about 90 percent by weight of acetonitrile based on the total weight of said dispersion, and wherein said water-rich phase comprises at least about 80 weight percent of water and less than 20 percent of acetonitrile based on the total weight of the water-rich phase.

* * * * *

UNITED STATES PATENT AND TRADEMARK OFFICE
CERTIFICATE OF CORRECTION

PATENT NO. : 4,865,991
DATED : September 12, 1989
INVENTOR(S) : Jeremy J. Mathers It is certified that error appears in the above-identified patent and that said Letters Patent is hereby corrected as shown below:

Column 2, line 10, change "311-325] of" to --311-325] of--;

Column 2, line 35, change "FIGURESS" to --FIGS.--.

Column 2, line 35 change "1band" to --1b and--.

Column 8, line 60 change "20" to --320--.

Column 9, line 22, change "4.4.11] which" to --4.4.11 which--.

Claim 7, column 10, line 41, change "clam" to --claim--.

Claim 10, column 10, line 52 change "2benzo-" to --2-benzo- --.

Signed and Sealed this

Fourth Day of December, 1990

Attest:

HARRY F. MANBECK, JR.

*Attesting Officer*     *Commissioner of Patents and Trademarks*